US006986751B2

(12) United States Patent
Villafana et al.

(10) Patent No.: US 6,986,751 B2
(45) Date of Patent: *Jan. 17, 2006

(54) GRAFTED NETWORK INCORPORATING A MULTIPLE CHANNEL FLUID FLOW CONNECTOR

(75) Inventors: Manuel A. Villafana, Plymouth, MN (US); William E. Palmquist, Plymouth, MN (US); Bruce Fletcher, Maple Grove, MN (US)

(73) Assignee: CABG Medical, Inc., Plymouth, MN (US)

(*) Notice: Subject to any disclaimer, the term of this patent is extended or adjusted under 35 U.S.C. 154(b) by 169 days.

This patent is subject to a terminal disclaimer.

(21) Appl. No.: 10/698,253

(22) Filed: Oct. 31, 2003

(65) Prior Publication Data
US 2005/0033218 A1 Feb. 10, 2005

Related U.S. Application Data

(63) Continuation-in-part of application No. 10/634,200, filed on Aug. 5, 2003.

(51) Int. Cl.
*A61M 5/00* (2006.01)
*A61B 17/08* (2006.01)
*A61F 2/06* (2006.01)

(52) U.S. Cl. .............. 604/9; 604/8; 606/158; 623/1.13; 623/1.16; 623/1.27; 623/1.35; 623/1.46

(58) Field of Classification Search ........ 604/4.01, 604/6.16, 7–9, 264, 523, 533, 532, 537, 538, 604/905, 284, 317, 322, 326; 128/898; 606/1, 606/8, 108, 151, 153, 155–158; 251/12, 251/24, 142, 148, 149, 151–155; 403/169, 403/170, 220, 265
See application file for complete search history.

(56) References Cited

U.S. PATENT DOCUMENTS

| | | | |
|---|---|---|---|
| 2,127,903 A | 8/1938 | Bowen |
| 2,258,720 A | 10/1941 | Saighman |
| 2,396,203 A | 3/1946 | Robinson |
| 2,455,859 A | 12/1948 | Foley |
| 2,671,444 A | 3/1954 | Pease, Jr. |
| 3,105,492 A | 10/1963 | Jeckel |
| 3,124,136 A | 3/1964 | Usher |
| 3,155,095 A | 11/1964 | Brown |
| 3,176,316 A | 4/1965 | Bodell |
| 3,176,690 A | 4/1965 | H'Doubler |
| 3,317,924 A | 5/1967 | Le Veen |
| 3,349,771 A | 10/1967 | Baer |

(Continued)

OTHER PUBLICATIONS

Neil, "Peripheral Circulation: Historical Aspects", Handbbok of Physiology, A Critical, Comprehensive Presentation of Physiological Knowledge and Concepts, vol. III, 1983, pp1-19.

*Primary Examiner*—Patricia Bianco
(74) *Attorney, Agent, or Firm*—Haugen Law Firm PLLP

(57) ABSTRACT

A grafted network including one or more graft segments for use in coronary bypass procedures and which are configured to operably transport bypass blood flow from a singular supply location to one or more delivery locations in the grafted network is provided in combination with one or more multiple channel blood flow connectors for directing such bypass blood flow in the grafted network to one or more vascular members requiring restorative blood flow thereto. The grafted network also preferably includes one or more devices for operably maintaining the grafted network under relatively high internal fluid pressure so as to continuously supply selective vascular members with adequate bypass blood flow.

18 Claims, 7 Drawing Sheets

U.S. PATENT DOCUMENTS

| | | |
|---|---|---|
| 3,435,823 A | 4/1969 | Edwards |
| 3,447,570 A | 6/1969 | Collins |
| 3,479,670 A | 11/1969 | Medell |
| 3,490,975 A | 1/1970 | Lightwood et al. |
| 3,527,220 A | 9/1970 | Summers |
| 3,538,917 A | 11/1970 | Selker |
| 3,545,008 A | 12/1970 | Bader, Jr. |
| 3,613,120 A | 10/1971 | McFarland, Jr. |
| 3,726,279 A | 4/1973 | Barefoot et al. |
| 3,730,186 A | 5/1973 | Edmunds, Jr. et al. |
| 3,938,528 A | 2/1976 | Bucalo |
| 3,993,078 A | 11/1976 | Bergentz et al. |
| 4,209,859 A | 7/1980 | Hoffman |
| 4,469,101 A | 9/1984 | Coleman et al. |
| 4,546,499 A | 10/1985 | Possis et al. |
| 4,601,718 A | 7/1986 | Possis et al. |
| 5,197,976 A | 3/1993 | Herweck et al. |
| 5,443,497 A | 8/1995 | Venbrux |
| 5,453,084 A | 9/1995 | Moses |
| 5,562,726 A | 10/1996 | Chuter |
| 5,588,436 A | 12/1996 | Narayanan et al. |
| 5,632,753 A | 5/1997 | Loeser |
| 5,797,879 A | 8/1998 | DeCampli |
| 5,807,258 A | 9/1998 | Cimochowski et al. |
| 5,824,064 A | 10/1998 | Taheri |
| 5,922,022 A | 7/1999 | Nash et al. |
| 5,967,989 A | 10/1999 | Cimochowski et al. |
| 5,968,053 A | 10/1999 | Revelas |
| 5,984,955 A | 11/1999 | Wisselink |
| 5,984,956 A | 11/1999 | Tweden et al. |
| 5,989,192 A | 11/1999 | Weijand et al. |
| 5,993,481 A | 11/1999 | Marcade et al. |
| 6,068,654 A | 5/2000 | Berg et al. |
| 6,165,185 A | 12/2000 | Shennib et al. |
| 6,241,761 B1 * | 6/2001 | Villafana .................... 623/1.13 |
| 6,241,764 B1 | 6/2001 | Villafana |
| 6,251,116 B1 | 6/2001 | Shennib et al. |
| 2003/0065377 A1 * | 4/2003 | Davila et al. ............... 623/1.13 |

* cited by examiner

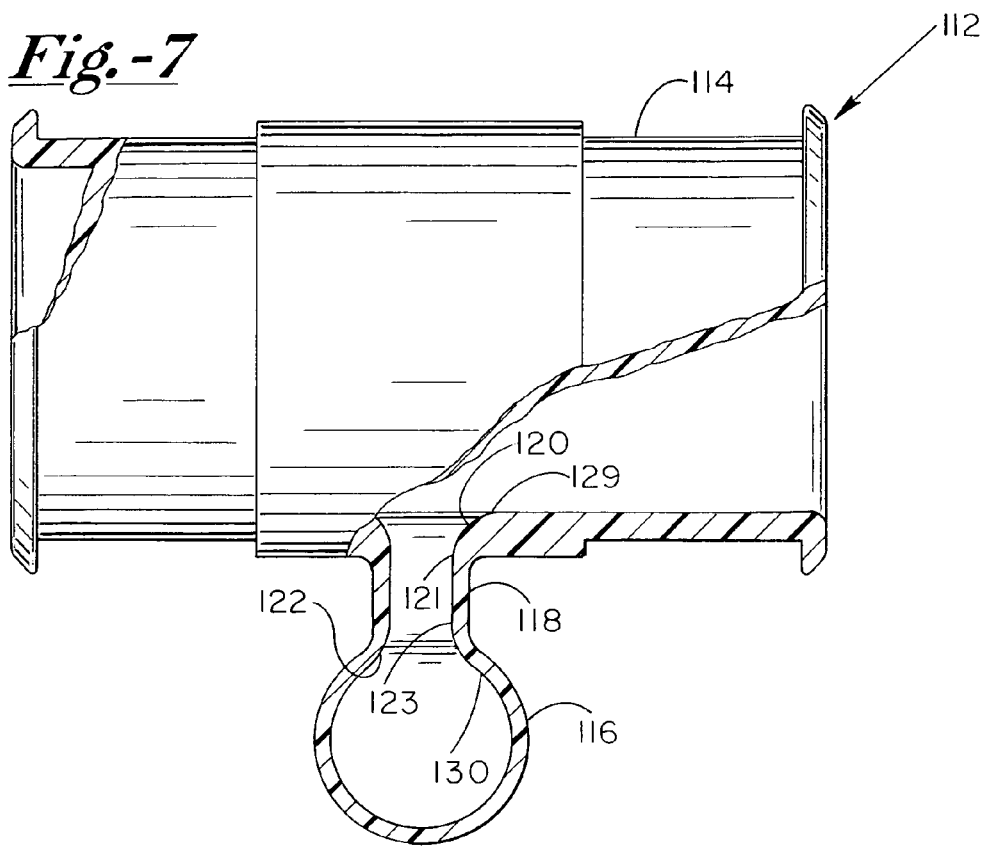
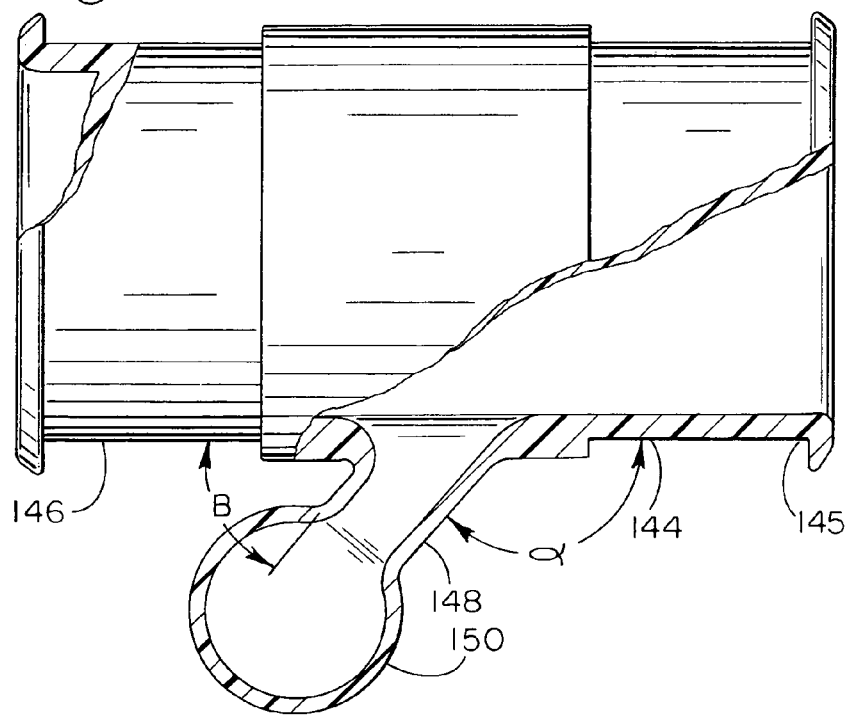

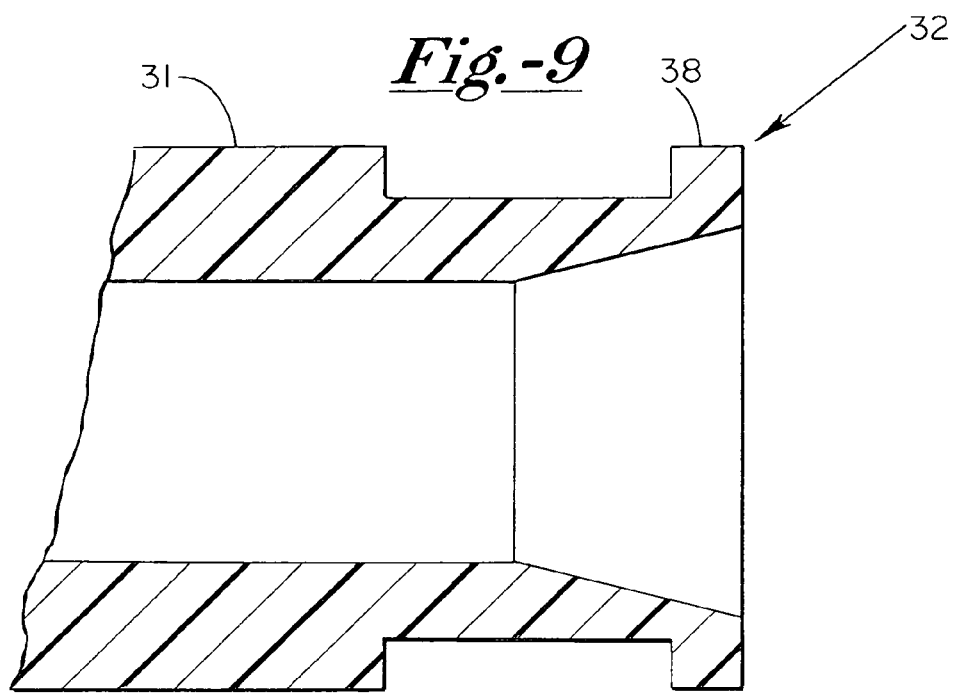
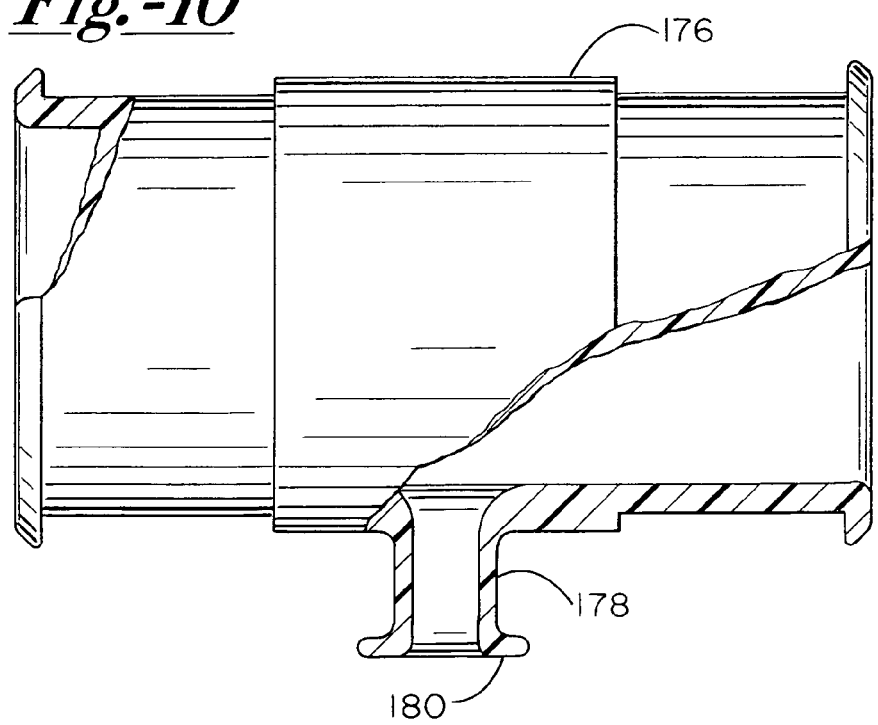

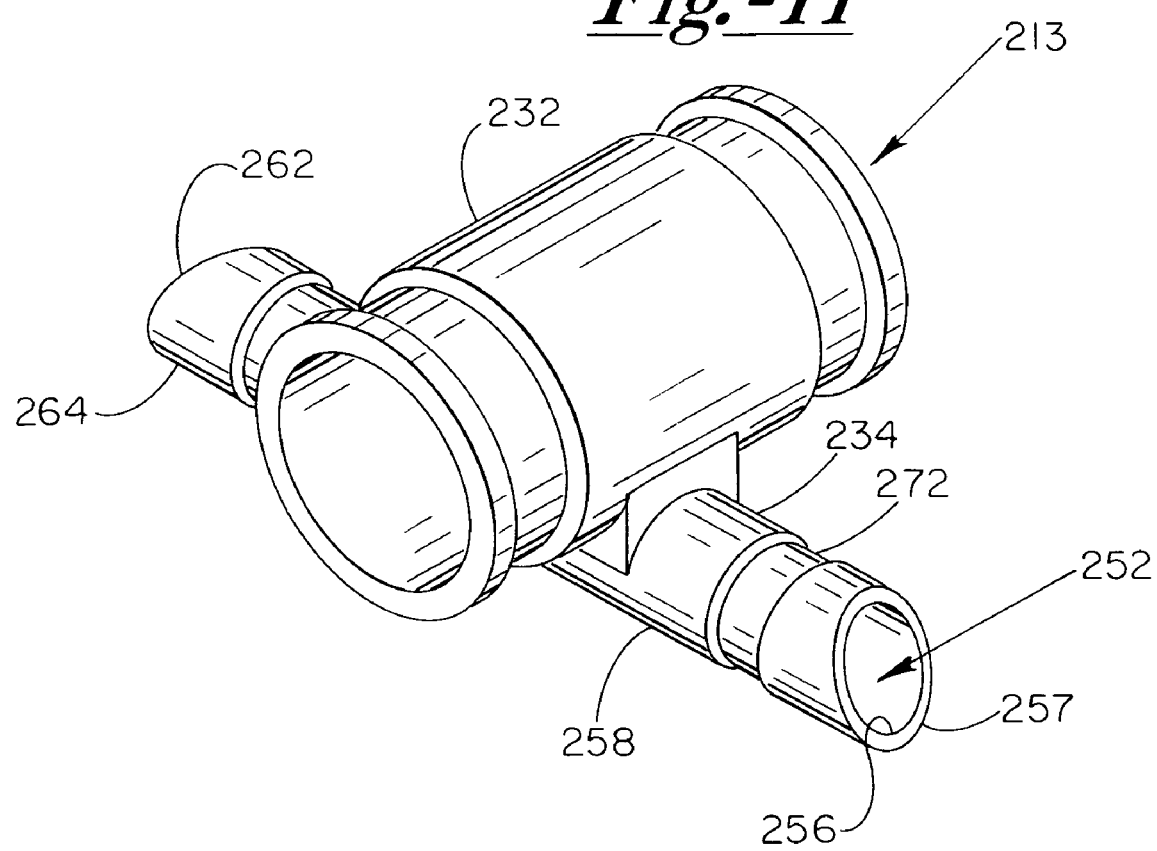

GRAFTED NETWORK INCORPORATING A MULTIPLE CHANNEL FLUID FLOW CONNECTOR

CROSS-REFERENCE TO RELATED APPLICATION

This application is a continuation-in-part of our co-pending application Ser. No. 10/634,200, filed Aug. 5, 2003, entitled "GRAFTED NETWORK INCORPORATING A MULTIPLE CHANNEL FLUID FLOW CONNECTOR", the contents of which is incorporated herein in its entirety.

FIELD OF THE INVENTION

The present invention relates to vascular graft networks generally, and more particularly to coronary graft networks incorporating one or more graft connectors that are specifically configured to efficiently transport bypass blood flow from a source to one or more delivery locations, which graft connectors may be directly implanted to the patient's vasculature at specific designated bypass locations.

BACKGROUND OF THE INVENTION

Coronary bypass surgery has become a common procedure, and is normally indicated for conditions requiring replacement and/or reconfiguration due to blockage of the coronary blood flow within a patient. To achieve such a bypass, grafts are surgically implanted to divert blood flow from a relatively high volume and pressure flow regime to a portion of the diseased vascular member downstream from the blockage therein. In typical bypass procedures, a section of the vascular system in a patient's body that has become impaired or inoperative through disease or other defects may be treated so as to improve flow to those portions previously being supplied with an inadequate or limited supply of blood. In order to create the graft bypass, biocompatible graft material is preferably employed, which graft material may be, for example, vascular members harvested from other portions of the patient's body or from other animals, or biocompatible artificial materials such as, for example, forms of polytetrafluoroethylene (commonly referred to as Teflon®).

While bypass procedures have been undertaken for some period of time, one particular and time consuming step is that of suturing the graft elements to respective portions of the patient's vasculature. Because of the physical properties of, in particular, artificial biocompatible graft material, suturing of such graft material is often times difficult to complete. The procedure is one which requires great dexterity, and when done at the site, is frequently in a zone with limited accessibility. Graft systems proposed to date have drawbacks with regard to ease of implantation and securement into the patient's vasculature.

An additional issue that is not satisfactorily addressed in existing bypass techniques is the inability of such techniques to effectively maintain flow and pressure from a blood flow source such as the aorta to the vascular member in which the bypass procedure is conducted. Specifically, the blood supply stream is typically in a high-pressure flow environment, while the vascular member subject to bypass flow is typically a low-pressure blood flow environment. Accordingly, the substantial pressure drop between the respective bypass blood flow locations generally results in low flow volumes to the artery or other vascular member to which bypass flow is directed. Previous attempts to provide sustained flow volumes to respective vascular members from a relatively high pressure source have been met with limited success, in that such systems proposed to date are difficult to manufacture and implement, and particularly difficult to produce positive reproducible implantation results. In particular, such prior systems fail to provides components that may be quickly and effectively implanted in the surgical process.

It is therefore a principle object of the present invention to provide a grafted network for consistently delivering sufficient blood flow volumes to respective vascular members in a bypass procedure.

It is a further object of the present invention to provide a grafted network incorporating distinct connector means for effectively channeling bypass blood flow into respective vascular members while minimizing damage to such vascular members and to such bypass blood flow.

It is a yet further object of the present invention to provide a grafted network incorporating one or more graft segments in combination with one or more distinct connector means for operably channeling bypass blood flow into respective vascular members.

It is another object of the present invention to provide a grafted network incorporating a plurality of graft segments, one or more distinct connector devices, and a flow restricting means for maintaining a desired level of blood flow pressure and volume through upstream graft segments and such connector devices into respective vascular members receiving bypass blood flow thereto.

It is a still further object of the preset invention to provide a grafted network which may be expediently surgically implanted within the patient's body.

SUMMARY OF THE INVENTION

By means of the present invention, a grafted network is provided for enabling one or more coronary bypass procedures to be performed from a single relatively high fluid pressure source location. In addition, the grafted network of the present invention allows the bypass procedure to be performed directly at particular sites in the targeted vascular members requiring bypass blood flow thereto, with each of the direct sites being supplied with blood flow from a common singular bypass blood flow stream. Moreover, the grafted network of the present invention includes means for maintaining the supply bypass blood flow stream at high pressure while minimizing any turbulent flow effects through the grafted network, so as to consistently provide adequate bypass blood pressure and flow volume to each of the vascular members receiving such flow.

In a particular embodiment of the invention, one or more graft segments configured to operably transport bypass blood flow from a singular supply location to one or more delivery locations in a grafted network are provided in combination with one or more multiple channel blood flow connectors for directing such bypass blood flow in the grafted network to one or more vascular members. The blood flow connectors are configured for coupling, for example, first and second graft segments to a first vascular member defining a first blood flow delivery location. The blood flow connector preferably includes a supply conduit and a delivery conduit integrally formed therewith and adjacently disposed with respect to one another, with the supply conduit and the delivery conduit each having a distinct lumen formed therewithin. The supply conduit of the blood flow connector preferably includes first and second opposed open ends having annular recessed portions and annular lips for operably attaching respective open ends of the first and second graft segments thereto. The supply lumen and the delivery lumen are fluidly connected to one another through cooperating apertures in respective outer walls of the supply conduit and the delivery conduit at an intersection therebetween so as to provide for immediate bypass blood flow from the supply lumen to the delivery lumen. The delivery conduit includes at least one open end portion extending from the intersection and beyond an outer circumferential dimension of the supply conduit outer wall, such that a first open end of the delivery conduit is laterally spaced from, and extends beyond, the supply conduit outer wall. The delivery conduit is preferably configured for operable implantation directly into the targeted vascular member so as to provide bypass blood flow thereto. The delivery conduit is also preferably specifically sized to provide internal structural support for the targeted vascular member when the delivery conduit is implanted therein. Such internal structural support is preferably provided without damage to the vascular member, as commonly occurs with stent devices.

In preferred embodiments of the present invention, a throttle device is provided in the grafted network downstream from the most-downstream bypass location, and adjacent to the low pressure vessel or anatomical site. The throttle device is operably coupled to the grafted network and is disposed between the last blood flow connector and a terminal delivery location for the grafted network of the present invention.

BRIEF DESCRIPTION OF THE DRAWINGS

FIG. 7 is a partial cut-away view of a blood flow connector device of the present invention.

FIG. 8 is a partial cut-away view of a blood flow connector device of the present invention.

FIG. 9 is a partial cross-sectional view of a portion of the blood flow connector device of the present invention.

FIG. 10 is a partial cutaway view of a blood flow connector device of the present invention.

FIG. 11 is a perspective view of a blood flow connector device of the present invention.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
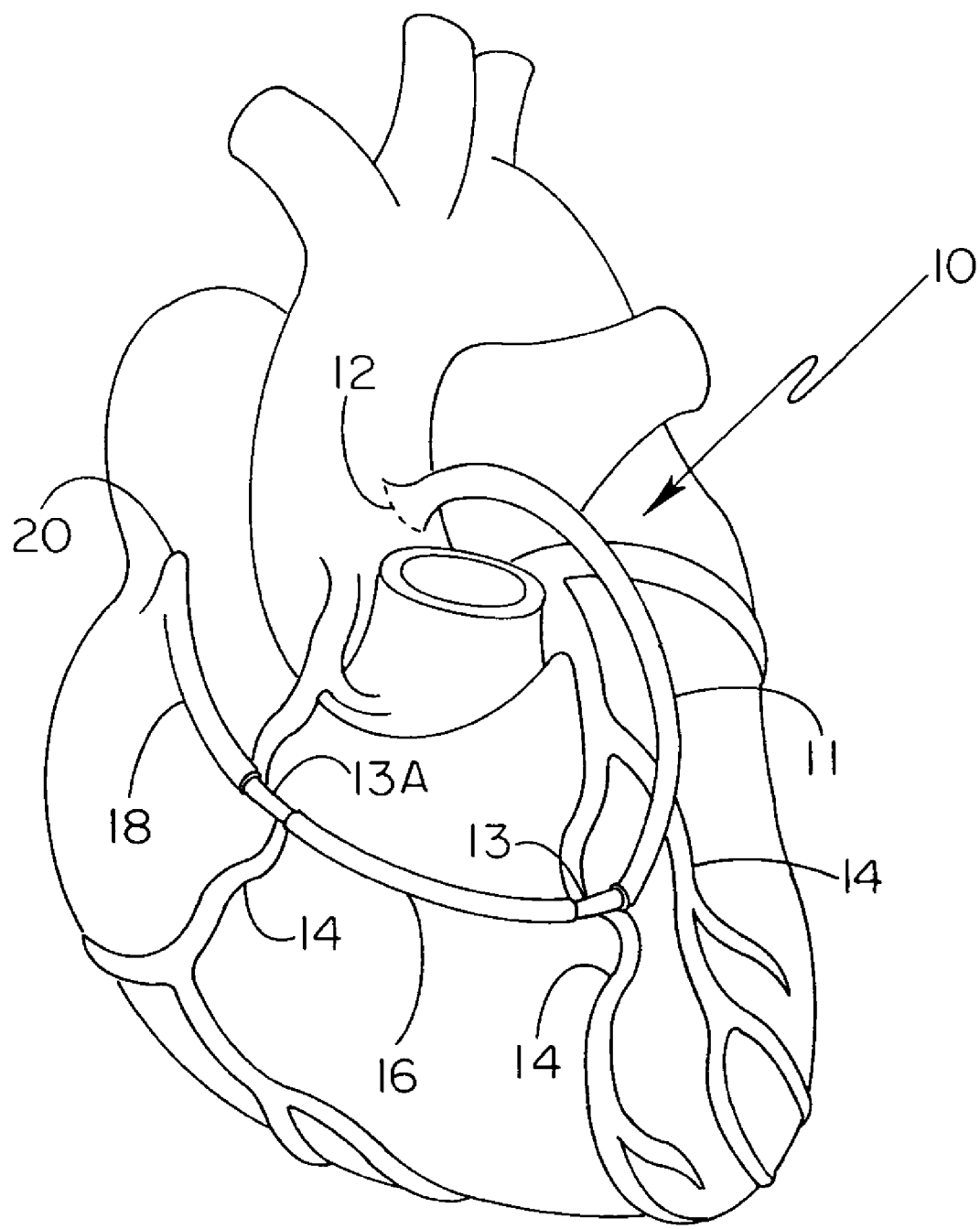
FIG. 1 is a front perspective view of a grafted network of the present invention employing a plurality of multiple channel blood flow connectors.

With reference to the enclosed drawing figures, and first to FIG. 1, a grafted network 10 includes a first graft segment 11 that is preferably attached by suture to a relatively high-pressure blood flow environment such as the aorta of a patient's heart, such as at location 12. Such location 12 comprises a singular supply location for directing blood through network 10 to one or more vascular members, such as coronary arteries 14.

As illustrated in FIG. 1, first graft segment 11 is preferably secured to connector 13, which is described in greater detail hereinbelow. Connector 13 is preferably configured so as to direct a portion of the blood flow passing from supply location 12 and through first graft segment 11 into a respective coronary artery 14. To accomplish the desired channeling of at least a portion of the blood flow, connector 13 preferably includes distinct conduits associated therewith, with at least one of such conduits being implantable into the respective vascular member, and particularly into coronary artery 14. Preferably, a second graft segment 16 is operably coupled to a downstream side of connector 13, with connector 13 being configured to convey a portion of the blood flow within first graft segment 11 to second graft segment 16. In the embodiment illustrated in FIG. 1, second graft segment 16 is operably coupled to a second connector 13A to thereby operably convey a portion of the blood flow within second graft segment 16 into a second artery 14 to which second connector 13A is operably coupled.

Figure 2:
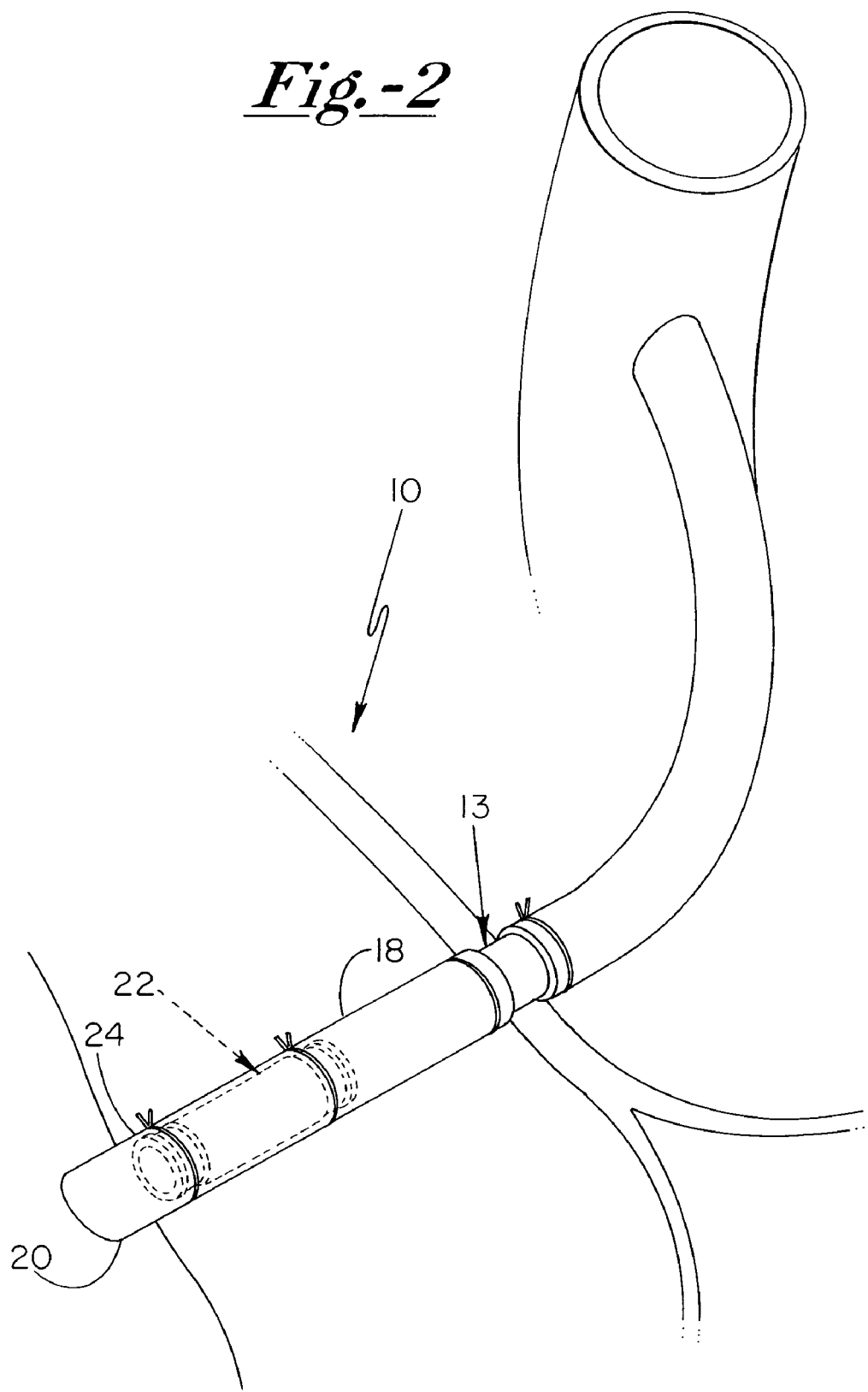
FIG. 2 is a schematic view of certain elements of the grafted network of the present invention.

In preferred embodiments of the present invention, grafted network 10 further includes a third graft segment 18 which is operably coupled to a downstream end of second connector 13A so as to transport remaining blood flow therefrom. In some embodiments, third graft segment 18 is operably coupled to a terminal delivery location 20 through suturing or the like. Terminal delivery location 20 may be a vascular member, and is preferably a relatively low pressure vessel or anatomical site such as an atrium or vena cava of the patient's heart. In preferred embodiments, however, and as illustrated in FIG. 2, a flow restricting means 22 is operably disposed between terminal delivery location 20 and the final and most downstream connector 13 in network 10. Flow restricting means 22 is preferably a distinct throttle device that is secured within a respective grafted segment 18, and is configured to restrict the volume of flow passing therethrough so as to maintain relatively higher pressure upstream therefrom. In addition, blood flow exiting flow restricting means 22 is preferably at a relatively low fluid pressure so as to blend into the blood channels formed by the atrium or vena cava without excessive turbulent flow effects. Of course, graft segment portion 24 which transports blood flow from a downstream end of flow restricting means 22 to terminal delivery location 20, carries only that blood which does not otherwise pass from network 10 to a respective coronary artery 14.

In some embodiments of the present invention, flow restricting means 22 may be secured between adjacent grafted segments, with a first grafted segment being operably coupled to a first open end of flow restricting means 22, with a second graft segment being operably coupled to a second downstream open end of flow restricting means 22. In still further embodiments of the present invention, flow restricting means 22 may be integrally formed within a respective graft segment 18, such that a portion of graft segment 18 includes a reduced internal diameter profile akin to that of flow restricting means 22. In such an embodiment, an entire workpiece may be formed through extrusion or other molding processes to produce a single element having a flow restricting means 22 integrally formed therewith.

Preferably, network 10 provides a means for efficiently performing one or more bypass procedures with a modular apparatus having any desired number of vascular member connectors 13 and graft segments fluidly coupling such connectors 13 to one another, as well as to at least a singular supply location 12, and preferably a terminal delivery location 20. The respective graft segments of network 10 are preferably fabricated from a biocompatible material that is somewhat elastic and is easy to manipulate by the surgeon. A particularly preferred material for use in manufacturing the graft segments is ePTFE, which is a form of polytetrafluoroethylene, and is widely known as a type of Teflon® material. The ePTFE segments are biocompatible, in that the body does not recognize such material as a "foreign" object, and therefore does not react negatively to its presence. Furthermore, the ePTFE material is capable of being formed into tubing of substantially any desired size, and extruded to a desired degree of surface smoothness. The biocompatible characteristics minimizes the likelihood of clot formation, while the intra-wall porosity improves the endothelialization of the ePTFE. Though variants of polytetrafluoroethylene are most desired in forming the graft segments of the present invention, other artificial or natural materials are also contemplated for use in the graft segments. For example, vascular material harvested from a patient's own body, or vascular materials harvested from other living beings may be used as implantable graft segments in network 10. A particular disadvantage of utilizing vascular materials harvested from patient's own body is that of additional recovery time and discomfort for the patient as well as progressive vessel disease incurred as a result of utilizing a vessel previously exposed to physiological effects. Accordingly, artificial biocompatible materials are most preferred to minimize the degree of invasiveness into the patient to accomplish the bypass procedures as to minimize the likelihood of natural blockage issues in the graft material.

An additional embodiment of the present invention is illustrated in FIG. 11, with connector 213 having a supply conduit 232 and a delivery conduit 234, which delivery conduit 234 includes at least first open end portion 258 having an open end 256. As shown in FIG. 11, first open end portion 258 is preferably formed at first open end 256 such that end 257 of delivery conduit 234 is substantially disposed along a plane in an angular relationship to a plane parallel to a perpendicular cross-section of a delivery lumen 252. Such an angular relationship is preferably between about 10 degrees and about 80 degrees with respect to a plane.

Connector 213 may further include a second open end portion 264 having a tapered second open end 262 which preferably substantially mirrors first open end 256. The respective tapered open ends 256, 262 provide for relatively easy insertion of delivery conduit 234 into a respective coronary artery, in that little or no arterial manipulation is required by the physician in order to insert delivery conduit 234 into place through an opening formed in the respective coronary artery. In particular, there is no operative need for additional instruments to dilate the target artery prior to delivery conduit 234 insertion therein.

As further illustrated in FIG. 11, delivery conduit 234 may include annular recessed portions 272 disposed in an outer surface thereof and adjacent to respective open ends 256, 262. Such recessed portions 272 are specifically configured to assist in obtaining a secure attachment between the target artery tissue and delivery conduit 234. Moreover, annular recessed portions 272 provide a locating zone at which to optionally suture arterial tissue thereto, in that such sutures may circumferentially bind such arterial tissue to respective annular recessed portions 272.

Figure 3:
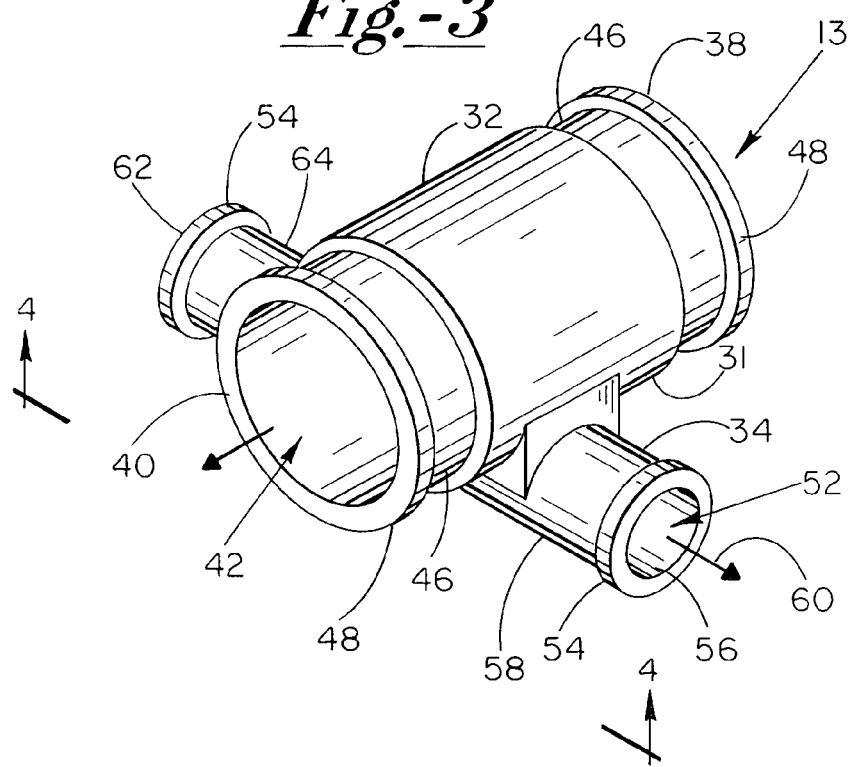
FIG. 3 is a front elevational view of a blood flow connector device of the present invention.

As is best illustrated in FIG. 3, blood flow connector 13 is preferably a distinct unit having a plurality of blood flow channels for operably directing and channeling blood flow to pre-determined locations, most preferably into targeted vascular members. Blood flow connector 13 includes a supply conduit 32 and a delivery conduit 34 integrally formed therewith and adjacently disposed with respect to one another. Though blood flow connector 13 is presently shown and described as having a single supply conduit and a single delivery conduit, variations of such a design are also contemplated by the present invention. Namely, such supply and/or delivery conduits may be branched into a plurality of distinct conduits, or, alternatively, a plurality of individual supply conduits and/or delivery conduits may be integrally formed in adjacent relationship with one another in a single connector unit.

Supply conduit 32 includes at least first and second opposed open ends 38, 40 which, in combination, define an axially extending supply lumen 42 defined within the inner annular wall of supply conduit 32. Preferably, a respective graft segment 11 is operably secured to first open end 38 of supply conduit 32.

In preferred embodiments, supply conduit 32 includes annular recessed portions or grooves 46 disposed in an outer surface thereof and adjacent to respective open ends 38, 40. Such recessed portions 46 are specifically configured to assist in obtaining a secure attachment between respective graft segments and supply conduit 32. As illustrated in FIG. 3, annular recessed portions 46 provide a locating zone at which to suture an open end of a respective graft segment therearound, in that such sutures may circumferentially bind open ends of the respective graft segments to respective annular recessed portions 46. Furthermore, such annular recessed portions 46, define respective outer lips 48 at respective open ends 38, 40 of supply conduit 32. In operation, sutures circumferentially retaining respective graft segments to annular recessed portions 46 are further held axially in place by outer lips 48 which create a friction fit with respect to the graft segments. Annular recessed portions 46 and outer lips 48, in combination, collectively form coupling means for assisting in the graft sutures process to supply conduit 32.

Delivery conduit 34 is preferably adjacently disposed to supply conduit 32, and preferably is integrally formed with supply conduit 32. Supply conduit 34 is preferably a hollow body, such that supply conduit 34 contains a distinct supply lumen 52 therewithin. In some embodiments of the present invention, delivery conduit 34 includes coupling means 54 akin to annular recessed portions 46 and outer lips 48. In other embodiments of the present invention, however, coupling means 54 on delivery conduit 34 includes an annular flange extension disposed about respective end portions of delivery conduit 34.

Preferably, delivery conduit 34 includes at least one open end 56 and end portion 58 laterally extending beyond an outer circumferential surface of supply conduit 32, such that when end portion 58 is operably positioned within a respective vascular member such as artery 14, the surgeon may quickly and easily suture artery 14 to end portion 58 without significant manipulation of connector 13, and without substantial interference from supply conduit 32 during the suturing process. In embodiments wherein delivery conduit 34 includes only one open end 56, all blood flow directed into the associated artery 14 exits through open end 56, as indicated by arrow 60. In other embodiments of the present invention, delivery conduit 34 includes first and second open ends 56, 62, with second end 62 forming a portion of end portion 64. Such embodiments are incorporated for applications in which bypass blood flow out from first and second end portions 58, 64 of delivery conduit 34 is desired.

Figure 4:
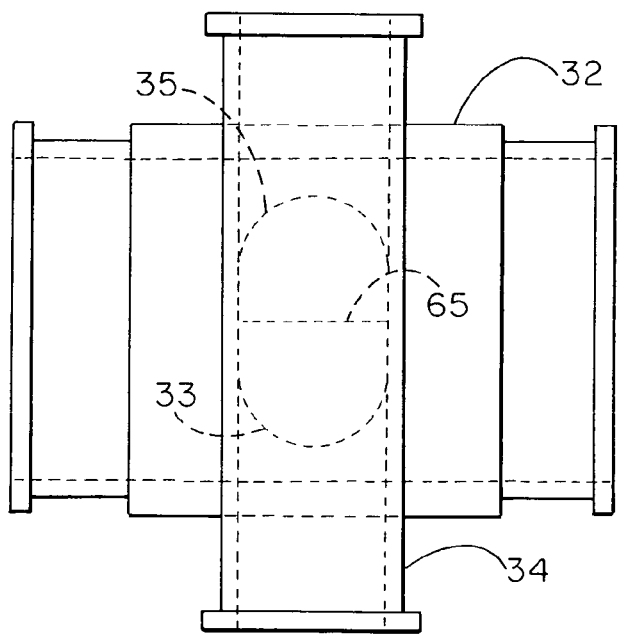
FIG. 4 is a bottom view of the connector device illustrated in FIG. 3.

As is best illustrated in FIG. 4, supply conduit 32 and delivery conduit 34 each include respective apertures 33, 35 disposed in integrally adjacent outer walls, such that respective apertures 33, 35 intersect and superimpose with one another such that supply lumen 42 and delivery lumen 52 are fluidly coupled to one another. Specifically, bypass blood flow entering first open end 38 of supply conduit 32 are transported in and through supply lumen 42, and to coordinating apertures 33, 35 of supply conduit 32 and delivery conduit 34. At least a portion of such bypass blood flow accordingly passes through coordinating apertures 33, 35, and correspondingly exits through one or more of open ends 56 and/or 62 of delivery lumen 52. Preferably, respective apertures 33, 35 are integrally formed with one another, so as to form a single unitary aperture fluidly coupling supply lumen 42 and delivery lumen 52. Such coordinating apertures preferably include radiused edges so as to minimize stresses placed upon blood passing therethrough, as well as to minimize turbulent fluid flow effects. Cooperating apertures 33, 35, in combination, define an intersection between supply conduit 32 and delivery conduit 34, with a central midpoint of such cooperating apertures 33, 35 defining a central intersection plane 65 referred to herein.

Blood flow connector 13 is preferably fabricated from a biocompatible material that is sufficiently strong and durable to withstand stress forces incorporated during implantation and eventually within the patient's body. A particularly preferred material for use in blood flow 13 is titanium, though a variety of other materials may be utilized instead. An alternative material for use in the fabrication of connector 13 is a polytetrafluoroethylene such as ePTFE. In addition, other biocompatible materials not specifically stated herein are also contemplated as alternative materials for use in blood flow connector 13 and/or flow restricting means 22.

As illustrated in FIGS. 1–2, connector 13 is preferably configured such that delivery conduit 34 may be directly implanted into a selected portion of the patient's vasculature, and preferably adjacent to, and downstream from, a blockage or other diseased portion of the particular vascular member. In such a manner, grafted network 10 may be implanted and surgically connected to the patient's vasculature directly, and without separate intravascular procedures. Therefore, the surgeon is able to create a distinct bypass (delivery) location in a selected vascular member by making a relatively small incision thereto at the selected site. The surgeon is then able to manipulate connector 13 so as insert delivery lumen 34 within the respective vascular member for blood conduction thereto. It is a particularly preferred aspect of the present invention to provide delivery conduit 34 with an outer dimension of a size similar to the internal diameter of the particular vascular member in which the bypass procedure is being conducted. Preferably, delivery conduit 34 is within about +/−20% of the corresponding inside diameter of the associated vascular member. The particular sizing described above with respect to delivery conduit 34 is preferred so as to obtain a snug friction fit between delivery conduit 34 and the associated vascular member. Due to the somewhat elastic nature of vascular members within the human body, it is desired to size substantially fixed-dimension elements of at least connector 13 similar to the corresponding vascular members so as to achieve a fluid-tight tissue fit connection therebetween. Such a fitment assists in permanently affixing the vascular member to grafted network 10 in addition to the sutures securing such vascular members to grafted network 10. Moreover, delivery conduit 34 is preferably a size so as to provide internal structural support to the corresponding vascular member when implanted therein. In some procedures, a separate and distinct expandable or fixed-configuration stent device is implanted into the vascular member in order to provide structural support to the vascular member after its structure has been compromised by a medical procedure performed thereon. Typical stent devices create substantial expansive forces on the respective vessel walls and in some cases generate excessive internal pressure on the vessel. Accordingly, delivery conduit 34 of the present invention acts both as a means for directing blood flow from grafted network 10 into a particular vascular member, as well as to structurally support such vascular member from therewithin without excessively straining the respective vessel wall. Such structural support operably maintains the associated vascular member in an open orientation and substantially prevents collapse thereof at the implantation location.

The foregoing description of the configuration and sizing of delivery conduit 34 may also be incorporated into supply conduit 32 for a preferred selected securement to respective graft segments. As indicated above, the preferred ePTFE material making up the respective graft segments is somewhat malleable in nature, and can therefore be configurationally modified by the surgeon during the implantation procedure. Preferably, respective open ends of the graft segments being operably secured to supply conduit 32 are modified with an appropriately-sized tool or a manual rolling manipulation that enlarges the inside diameter of an end portion of the respective graft segments being fitted onto respective ends on supply conduit 32. In such a manner, latent restorative forces within the respective graft segments act to compress upon respective outer surfaces of supply conduit 32, so as to obtain a snug connection thereto.

In preferred embodiments of the present invention, one or more components of the apparatus of the present invention may be coated on at least inner surfaces thereof with biocompatible material or made of mixed biocompatible material to further reduce any biological incompatibility issues. In particular, such biocompatible and/or drug eluting coatings are preferably disposed on at least inner surfaces of connector 13, though such biocompatible coatings may be placed upon any or all surfaces of grafted network 10. A particular biocompatible coating contemplated for use in the present invention includes a multi-layer biocompatible coating including silane, polyvinylpyrrolidine (PVP), heparin, and a photo-reactive cross-linking agent. In particular, a first layer contains isopropylalcohol (IPA), a second layer having a hydrophilic material such as PVP and IPA, and a third layer having PVP and heparin. Such a biocompatible coating is for exemplary purposes only, and does not restrict the present invention from utilizing a wide variety of biocompatible coatings on inner and outer surfaces of respective components of the present invention. For example, carbon coatings may be utilized on bio-compatible as well as non biocompatible components of the present invention through vapor deposition or other known coating processes.

Other biocompatible materials may be utilized for various elements of the present invention, including certain mixed, or co-extruded materials. A particular example of a co-extruded biocompatible material useful in respective components of the present invention is co-extruded resins of ePTFE and carbon. In addition, pyrolytic carbon may be utilized as a biocompatible material in such components.

As shown in FIG. 9, at least first end 38 of supply conduit 32 is preferably tapered such that the thickness of supply conduit 32 at first end 38 is less than about 50% of the thickness of central portion 31 of supply conduit 32. Such a tapered end is an important aspect of the present invention, and is specifically configured for reducing flow stresses on the fluid, as well as minimizing imposition of turbulent flow characteristics to the fluid flow stream. By minimizing such effects, the blood flow passing through connector 13 is less likely to be damaged and/or to coagulate or clot, which could potentially pose a health threat to the patient. Accordingly, the tapered configuration of the present invention specifically enables smooth flow transitions from respective graft segments into, and through connector 13, as well as eventually into the respective vascular members of the patient. In addition to tapering first end 38 of connector 13, the present invention contemplates tapering second end 40 of supply conduit 32, as well as open ends of delivery conduit 34 and flow restricting means 22. Various combinations of tapered ends of respective components of the present invention may be utilized as desired.

An additional aspect of the present invention for assisting and minimizing potentially deleterious effects to blood flow passing through various components of network 10 is in the preferred surface finishing of, in particular, flow connector 13. Specifically, the surface finish of at least inner surfaces of connector 13 and preferably of flow restricting means 22, is about 20–30 μ inches, and more preferably between about 24 and about 28 μinches. The above-stated level of surface smoothness is advantageous in the present invention for minimizing hemolysis in the blood flow passing therethrough.

Figure 5:
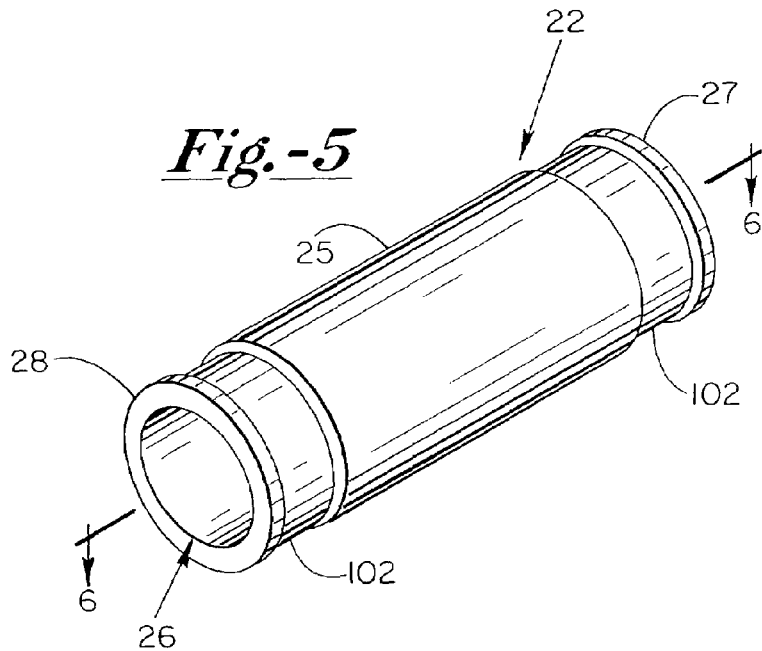
FIG. 5 is a front elevational view of a throttle device of the present invention.
Figure 6:
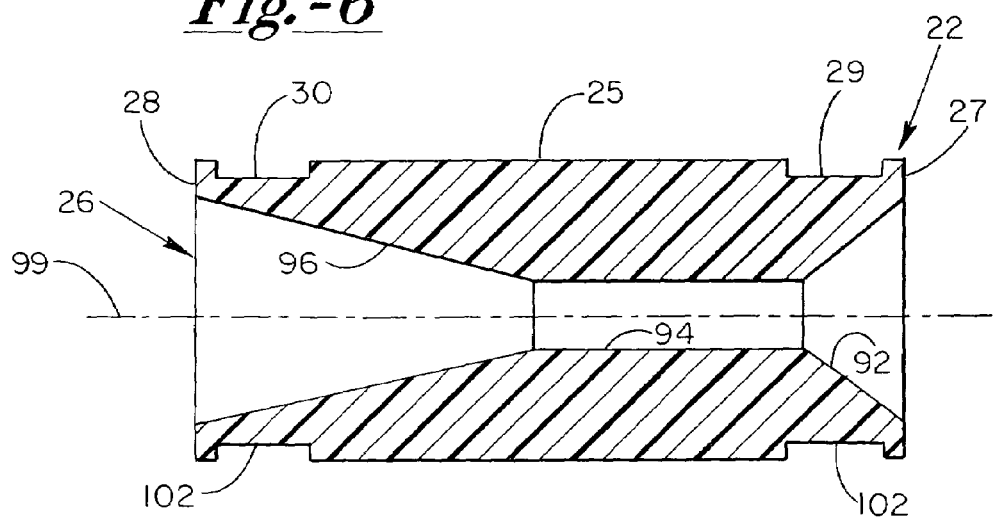
FIG. 6 is a side cross-sectional view of the throttle device illustrated in FIG. 5.

As is illustrated in FIG. 2 and in FIGS. 5–6, grafted network 10 preferably includes a flow restrictor means 22 having a contoured inner diameter so as to obtain a throttling effect to fluid passing therethrough. The contoured inner dimension of flow restricting means 22 is shown in dashed lines in FIG. 2, and is best represented in the cross-sectional view of FIG. 6. Flow restricting means 22 is preferably a distinct unit having an outer surface 25 and an open channel 26 axially extending therethrough. Flow restricting means 22 further includes first and second ends 27, 28, with flow being directed through restricting means 22 from first end 27 through second end 28. Preferably, flow restricting means 22 includes a converging tapered portion 92 extending from a first end portion 29 to a central throttle portion 94. As shown in FIG. 6, central throttle portion 94 extends between converging inlet tapered portion 92 to diverging outlet tapered portion 96, which diverging outlet taper portion 96 extends to second end portion 30 of flow restricting means 22. Although flow restricting means 22 is described as having "tapered" portions for providing desired flow characteristics, the present invention contemplates a variety of inlet portion and outlet portion configurations including parabolic or other formations, so long as inlet portion 92 includes a converging inner diameter, and outlet portion incorporates a diverging inner diameter for flow restricting means 22.

The inner diameter configuration through flow restricting means 22 is preferably designed so as to create a substantial flow pressure decrease between inlet end 27 and outlet end 28, as well as to create substantial back pressure into grafted network 10 upstream from flow restricting means 22. Such objectives are accomplished by reducing the diameter through which fluid flow may pass as it exits grafted network 10. However, it is preferred that the flow restricting means enable such pressure characteristics while maintaining a substantially laminar flow regime throughout flow restricting means 22. Accordingly, the inner diameter profile of flow restricting means 22 is specifically configured so as to maximize pressure drop therethrough while maintaining substantially laminar flow regime. In particular, inlet taper portion 92 is tapered between about 30 to about 40° with respect to a central axis 99 of flow restricting means 22, and more preferably between about 35°–40°. Outlet diverging taper portion 96 of the present invention is preferably angled between about 10° and about 20° with respect to axis 99, and more preferably about 12°–15° with respect to axis 99. Disposed between such inlet taper portion 92 and outlet taper portion 96 is throat portion 94, which is a substantially constant-diameter section of open channel between about 1.5 to about 2.0 mm, and more preferably between about 1.6 and about 1.8 mm in diameter. In other embodiments of the present invention, however, throat portion 94 may be somewhat convergent or divergent in inner diameter, or both, such that none or only a portion of throat portion 94 is a constant diameter.

In preferred embodiments of the present invention, fluid flow passing through flow restricting means 22 loses between about 90 and 95% of the energy initially carried by the fluid upon exit from source location 12. Accordingly, flow restrictor means 22 creates a substantial pressure drop from inlet 27 to outlet 28, thereby effectively maintaining a constant fluid pressure in network 10 upstream from flow restricting means 22, which pressure is substantially equal to the fluid flow pressure within the relatively high fluid pressure source. In other words, the relatively high fluid pressure to relatively low fluid pressure network provided by flow restrictor means 22 of the present invention enables network 10 to maintain relatively high fluid flow throughout the system. Accordingly, the one or more vascular members being supplied with bypass blood flow are insured of having adequate source flow from network 10 to satisfy the needs of the particular vascular member.

In some existing systems for bypass procedures, graft segments are utilized to directly couple an aortic blood source to a respective vascular member requiring bypass blood flow thereto. Due to the generally low pressure environment of the arteries receiving bypass blood flow, blood is not typically supplied under pressure throughout the graft segment. As such, bypass blood flow into the respective arteries can be less than adequate due to the low fluid pressure within the graft segment. By contrast, network 10 of the present invention is maintained under relatively high pressure due to the specifically configured flow restraining means 22. Accordingly, bypass blood flow is immediately available to respective vascular members 14 through connectors 13 when needed. An additional advantage inherent in network 10 of the present invention is due to the relatively high fluid pressure maintained therewithin. In many current systems, stand-alone graft segments must be spirally reinforced to maintain a predetermined configuration, particularly during times of relatively low internal fluid pressure. Since the respective graft segments of network 10 of the present invention are consistently maintained at relatively high internal fluid pressure, no spiral reinforcement of respective graft segments is required herein. Accordingly, the thickness, and therefore workability and malleability, of the graft segment material may be significantly reduced. Moreover, such reduced thickness graft material further results in cost savings over conventional systems.

As described above, flow restricting means 22 may preferably include annular recessed portions 102 disposed on an outer surface thereof adjacent to first and second ends 27, 28.

Such annular recessed portions act as locating means for assisting a technician in securing flow restricting means within a respective graft segment by providing locations at which sutures or other securing means may be fixedly positioned. Flow restricting means 22 is preferably a distinct body that is operably positioned and secured within a respective graft segment, such as graft segment 18, at a location adjacent to terminal delivery location 20. The distinct body of flow restricting means 22 may be selectively positioned at desired locations within a respective graft segment, such that network 10 is modifiable for particular implantation procedures.

In other embodiments of the present invention, open ends of respective graft segments are coupled to first and second ends 27, 28 of flow restricting means 22. Such graft segment ends may preferably be expanded outwardly with the use of a tool having a specific predetermined diameter or a rolling manual manipulation, such that the resulting internal diameter of respective open ends of the graft segments coupled to flow restrictor means 22 through a snug interference fit. Of course, such graft segments are permanently secured to first and second ends 27, 28 of flow restricting means 22 through sutures or other permanent attaching means, such as glue or the like.

In still further embodiments of the present invention, flow restricting means 22 may be integrally formed with a respective graft segment, in that the graft segment and flow restricting means 22 share common materials and outer surfaces. In such an embodiment, the respective graft segment is provided as being substantially longer than is necessary in typical implantation procedures, such that the surgeon may cut the length of the unit to properly fit within network 10 of the present invention.

Flow restricting means 22 is preferably fabricated from a biocompatible material such as ePTFE, but may instead be fabricated from other durable and biocompatible materials, including certain metals. In addition, flow restricting means 22 may include one or more biocompatible coatings disposed on at least inner surfaces thereof for enhancing its compatibility within the body of a patient.

Additional embodiments of multiple channel fluid flow connectors of the present invention are illustrated in FIGS. 7–8. Ass shown in FIG. 7, flow connector 112 includes a supply conduit 114 and a delivery conduit 116, with supply conduit 114 and delivery conduit 116 being coupled via intermediate, conduit 118. Preferably, intermediate conduit 118 forms an open passageway between supply conduit 114 and delivery conduit 116 such that supply conduit 114 and delivery conduit 116 are fluidly coupled to one another via intermediate conduit 118. Preferably, intermediate conduit 118 includes radiused transition points forming flared ends 120, 122 for transporting blood flow therethrough with minimal deleterious effects thereon. In particular flared ends 120, 122 extend outwardly from an annular apex 121, 123 to respective annular outer ends 129, 130, with such annular outer ends 129, 130 having a diameter exceeding the diameter of transfer conduit 118 by between about 0.25 and about 1.5 mm. Such a configuration minimizes turbulent flow effects, as well as transitional corners where damage to blood may occur.

A further alternative embodiment is illustrated in FIG. 8, wherein transfer conduit 148 is angled with respect to supply conduit 144 in an orientation such that an obtuse angle a of between about 100° and 120° is formed between transfer conduit 148 and first inlet open end 145 of supply conduit 144. Correspondingly, an acute angle β of between about 60° and about 80° is formed between transfer conduit 148 and second outlet end 146 of supply conduit 144. In the embodiment illustrated in FIG. 8, transfer conduit 148 is so angled such that in-flow of fluid is at least partially directed into delivery conduit 150 through transfer conduit 148 without having to undergo a substantially right-angle flow transition. Thus, fluid flow passing through transfer conduit 148 undergoes a reduced degree of stress imparted thereon to reach delivery conduit 150.

An additional alternative embodiment of the present invention is illustrated in FIG. 10, and shows a flared outer end of transfer conduit 178. Such a flared outer end 180 assists in minimizing turbulent flow effects as blood flow is routed from supply conduit 176 into the targeted vascular member via transfer conduit 178.

Referring back to FIGS. 3 and 4, first end portion 58 may be somewhat longer than second end portion 62, and may be between about 1 and 4 mm longer than second end portion 62. Such a, configuration assists the surgeon in inserting delivery conduit 34 into the targeted vascular member 14 by reducing the incision size into vascular member 14. In operation, the surgeon may insert relatively longer end portion 58 into vascular member 14, and then simply "drop" second end portion 62 therein for complete insertion. In other embodiments of the present invention, second end portion 62 may be relatively longer than first end portion 58, as measured from intersection plane 65.

In some embodiments of the present invention, at least delivery conduit 34 is fabricated from a selectively expansive material, such that when delivery conduit 34 is implanted within a particular vascular member 14, the diametrical dimension thereof may be selectively expanded so as to obtain a fluid-tight interference fit within the respective vascular member 14. Such a selectively expansive material may be in a mesh configuration, and may be, for example, nitanol. Other components of the present invention may also or instead be fabricated from a selectively expansive material.

An additional embodiment of the present invention provides for a rotation means disposed between supply conduit 32 and delivery conduit 34, wherein delivery conduit 34 may be selectively rotated with respect to supply conduits 32, whereby specific alignment between network 10 and a particular vascular member 14 is less critical, due to the fact that delivery conduit 34 may be rotated into alignment with such vascular member 14 without disturbing grafted network 10.

In preferred embodiments of the present invention, supply conduit 32 is between about 2 mm and about 8 mm in external diameter, and delivery conduit 34 is between about 0.5 mm and about 5 mm in external diameter. In a particularly preferred embodiment of the present invention, supply conduit 32 has an external diameter, of about 6 mm, and delivery conduit 34 has an external diameter of about 3 mm.

In accordance with the present invention, one or more graft segments are provided for each bypass procedure. In addition, at least one multiple channel fluid flow connector is provided comprising biocompatible material and includes an integrated supply conduit and delivery conduit for channeling blood flow from a relatively high pressure source to a location in, for example, a coronary artery where blood flow correction is needed. The connector devices are typically dual-lumen which provides for direct channeling from the supply conduit to the delivery conduit, and consequently to the targeted vascular member. In the dual-lumen structure of the present invention, a relatively large diameter lumen is employed for that portion of the connector device which is in direct communication with the aortic or other high pressure source, and with the delivery lumen typically being of somewhat lesser overall diameter and being designed for insertion into a slit formed in the targeted-vascular member requiring bypass.

In preferred embodiments of the present invention, at least one graft segment is pre-attached to an open end of connector 13, and is of a length which is more than ample for the contemplated use. For example, first graft segment 11 is preferably pre-attached to first end 38 of supply conduit 32 prior to surgery, and preferably prior to shipment from the manufacturing facility. First graft segment 11 is consequently made substantially longer than necessary for connection between vascular member 14 and source location 12, such that the surgeon may cut first graft segment 11 to size during the surgical process. Thus, the surgeon is able to cut the graft segment to a desired and required length in the course of the procedure, while at the same time not having to disturb the integrity of the previously-prepared secure junction between first graft segment 11 and connector 13.

In the course of the overall procedure, terminal end 20, including graft segment 24, are secured in place at the vena cava or other low-pressure site, while continuing the process in the direction of the source, which is normally the aorta. Attachments are made in accordance with conventional protocol, with connector 13 being coupled through a slit formed in the pertinent vascular member to provide bypass flow thereto.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. In combination with one or more graft segments configured to operably transport bypass blood flow from a singular supply location to one or more delivery locations in a grafted network, an apparatus for directing such bypass blood flow in said grafted network to one or more vascular members, said apparatus comprising:

a multiple channel blood flow connector for coupling at least a first graft segment to a first vascular member comprising a first blood flow delivery location, said flow connector including a supply conduit and a delivery conduit integrally formed therewith and adjacently disposed with respect to one another, with said supply conduit and said delivery conduit each having distinct lumen formed therewithin, said supply conduit having a first open end being operably coupled to a first respective open end of such first graft segment, said supply lumen and said delivery lumen being fluidly connected to one another through cooperating apertures in respective outer walls of said supply conduit and said delivery conduit at an intersection therebetween so as to provide for immediate bypass blood flow from said supply lumen to said delivery lumen, said delivery conduit having at least a first open end portion extending from said intersection and beyond a first perpendicular tangential plane of said supply conduit outer wall at a lateral side thereof with respect to said intersection, such that a first open end of said delivery conduit is laterally spaced from said supply conduit outer wall, an outer wall of said delivery conduit being formed at said first open end substantially along a plane in angular relationship with a plane parallel to a perpendicular cross-section of said delivery lumen, such angular relationship being between about 10 degrees and about 80 degrees therebetween, said first open end of said delivery conduit being configured for operable implantation directly into the first vascular member so as to provide bypass blood flow thereto, said delivery conduit being specifically sized to provide internal structural support for the first vascular member when said delivery conduit is implanted therein.

2. An apparatus as in claim 1 wherein the first graft segment is operably coupled to the blood flow supply location and said first open end of said supply conduit of said flow connector, and a first end of a second graft segment is operably coupled to a second open end of said supply conduit of said flow connector.

3. An apparatus as in claim 2, including a flow restricting means disposed downstream from said flow connector and operably coupled to said grafted network adjacent a terminal delivery location thereof opposite the supply location.

4. An apparatus as in claim 3 wherein said flow restricting means includes first and second open ends operably coupled to respective graft segments in said grafted network, with one of said respective graft segments extending between said flow restricting means and said terminal delivery location.

5. An apparatus as in claim 4 wherein said blood flow supply location is an aorta, and said terminal blood flow delivery location is an atrium or vena cava of a patient.

6. An apparatus as in claim 3, including one or more biocompatible coatings disposed on at least inner surfaces of said flow restricting means.

7. An apparatus as in claim 6 wherein at least one of said biocompatible coatings comprises silane, polyvinylpyrrolidine, heparin, and a photo-reactive cross-linking agent.

8. An apparatus as in claim 1, including one or more biocompatible coatings on at least inner surfaces of said flow connector.

9. An apparatus as in claim 8 wherein at least one of said biocompatible coatings comprises silane, polyvinylpyrrolidine, heparin, and a photo-reactive cross-linking agent.

10. An apparatus as in claim 1 wherein said delivery conduit includes a second end portion having a second end, with said second end portion extending from said intersection in a direction divergent from said first end portion of said delivery conduit.

11. An apparatus as in claim 10 wherein said first end of said delivery conduit is open, and said second end is closed.

12. An Apparatus as in claim 1 wherein said first open end of said supply conduit is tapered such that the thickness of said supply conduit outer wall at said first open end is less than about 50% of the thickness of said supply conduit outer wall at locations between said first open end and said intersection.

13. An apparatus as in claim 1 wherein at least said first open end of said delivery conduit is tapered such that the thickness of said delivery conduit outer wall at said first open end is less than about 50% of the thickness of said delivery conduit outer wall at locations between said first open end and said intersection.

14. An apparatus as in claim 1 wherein said cooperating apertures have radiused edges.

15. An apparatus as in claim 1, including a biocompatible coating disposed on at least inner surfaces of selected graft segments.

16. An apparatus as in claim 1 wherein said supply conduit has an external diameter of up to about 8 mm and said delivery conduit has an external diameter of up to about 5 mm.

17. An apparatus as in claim 1 wherein said first end portion of said delivery conduit is at least 1 mm longer than said second end portion of said delivery conduit as measured from said intersection.

18. An apparatus as in claim 1 wherein at least said delivery conduit is formed from a selectively expansive material for providing an interference fit between said delivery conduit and the vascular members sufficient to assist in forming a liquid-tight seal therebetween.

* * * * *